(12) United States Patent
Ballard et al.

(10) Patent No.: US 11,331,123 B2
(45) Date of Patent: May 17, 2022

(54) SPINAL IMPLANT

(71) Applicant: Warsaw Orthopedic, Inc., Warsaw, IN (US)

(72) Inventors: Rodney Ray Ballard, Lakeland, TN (US); William Alan Rezach, Covington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 100 days.

(21) Appl. No.: 16/202,401

(22) Filed: Nov. 28, 2018

(65) Prior Publication Data

US 2020/0163701 A1 May 28, 2020

(51) Int. Cl.
*A61B 17/70* (2006.01)
*A61B 17/86* (2006.01)
*A61B 17/68* (2006.01)

(52) U.S. Cl.
CPC ........ *A61B 17/7032* (2013.01); *A61B 17/866* (2013.01); *A61B 17/8625* (2013.01); *A61B 17/8695* (2013.01); *A61B 2017/681* (2013.01); *A61B 2017/8655* (2013.01)

(58) Field of Classification Search
CPC .................................................. A61B 17/7032
See application file for complete search history.

(56) References Cited

U.S. PATENT DOCUMENTS

| | | | |
|---|---|---|---|
| 7,850,717 B2 | 12/2010 | Dewey et al. | |
| 2008/0177331 A1 | 7/2008 | Perez-Cruet et al. | |
| 2010/0042167 A1 | 2/2010 | Nedosky et al. | |
| 2011/0009911 A1* | 1/2011 | Hammill, Sr. | A61B 17/7037 606/308 |
| 2011/0112582 A1* | 5/2011 | Abdelgany | A61B 17/7037 606/267 |
| 2011/0172798 A1 | 7/2011 | Staiger | |
| 2012/0059426 A1* | 3/2012 | Jackson | A61B 17/7008 606/300 |
| 2013/0310942 A1* | 11/2013 | Abdou | A61B 17/7079 623/17.16 |
| 2013/0338715 A1* | 12/2013 | Daly | A61B 17/7032 606/263 |
| 2015/0018956 A1 | 1/2015 | Steinmann et al. | |
| 2015/0032159 A1 | 1/2015 | Beger et al. | |
| 2015/0223907 A1 | 8/2015 | Kieser | |
| 2015/0313658 A1 | 11/2015 | Kolb | |
| 2016/0157908 A1* | 6/2016 | Cawley | A61B 17/7032 606/301 |
| 2016/0367371 A1 | 12/2016 | de Beaubien | |
| 2017/0049481 A1* | 2/2017 | Faulhaber | A61B 17/7035 |
| 2017/0165077 A1 | 6/2017 | Mcdonnell | |
| 2017/0245851 A1 | 8/2017 | Biedermann et al. | |
| 2018/0028242 A1 | 2/2018 | Parekh et al. | |
| 2018/0042702 A1 | 2/2018 | Stuebinger | |
| 2018/0092670 A1* | 4/2018 | Crossgrove | A61B 17/7032 |

* cited by examiner

*Primary Examiner* — Tessa M Matthews
(74) *Attorney, Agent, or Firm* — Sorell, Lenna & Schmidt, LLP

(57) ABSTRACT

A bone screw includes a shaft including at least one thread having an external thread form and an implant receiver. A ring includes a mating surface engageable with the implant receiver and an outer surface, at least a portion of the outer surface having a coarse configuration to promote tissue on-growth with the outer surface. In some embodiments, systems, spinal constructs, surgical instruments and methods are disclosed.

19 Claims, 3 Drawing Sheets

SPINAL IMPLANT

TECHNICAL FIELD

The present disclosure generally relates to medical devices for the treatment of spinal disorders, and more particularly to a spinal implant system including a ring disposable with a spinal implant to enhance fixation strength with tissue and/or facilitate bony on-growth with the spinal implant.

BACKGROUND

Spinal pathologies and disorders such as kyphosis, scoliosis and other curvature abnormalities, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including rods and bone fasteners are often used to provide stability to a treated region. Rods redirect stresses away from a damaged or defective region while healing takes place to restore proper alignment and generally support the vertebral members. The rods may be attached via the fasteners to the exterior of vertebral members. This disclosure describes an improvement over these prior technologies.

SUMMARY

In one embodiment, a bone screw is provided. The bone screw includes a shaft including at least one thread having an external thread form and an implant receiver. A ring includes a mating surface engageable with the implant receiver and an outer surface, at least a portion of the outer surface having a coarse configuration to promote tissue on-growth with the outer surface. In some embodiments, systems, spinal constructs, surgical instruments and methods are disclosed.

In one embodiment, a spinal implant compression ring is provided. The compression ring comprises a body. A first surface configured for engagement with a receiver of a bone screw. A second surface configured for engagement with a head of a bone screw. An outer surface having a coarse configuration to promote tissue on-growth with the outer surface.

In one embodiment, the bone screw comprises a shaft including at least one thread having an external thread form. An implant receiver. A compression ring includes a mating surface engageable with the implant receiver and an outer surface, at least a portion of the outer surface having a porous layer to promote tissue on-growth with the outer surface.

BRIEF DESCRIPTION OF THE DRAWINGS

The present disclosure will become more readily apparent from the specific description accompanied by the following drawings, in which.

DETAILED DESCRIPTION

Figure 1:
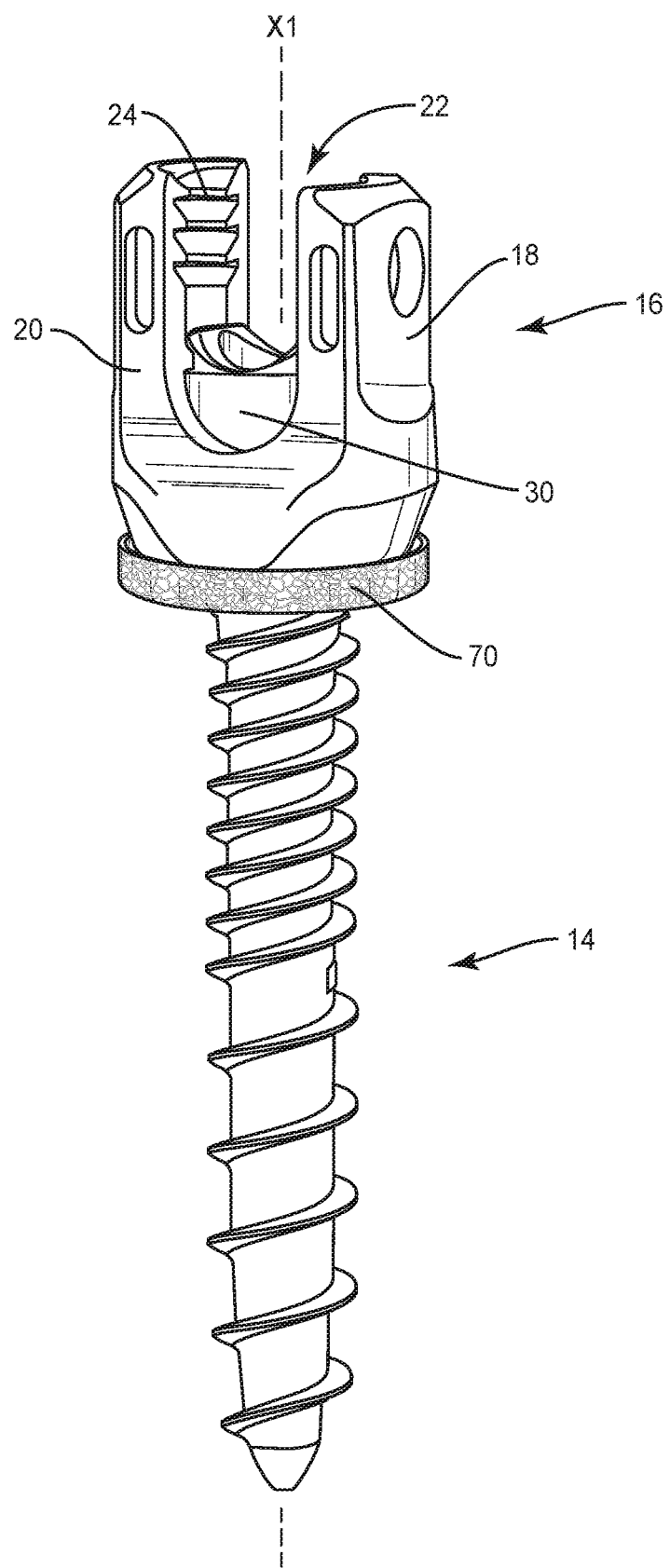
FIG. 1 is a perspective view of components of one embodiment of a system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a ring disposable with a spinal implant to enhance fixation strength with tissue and/or facilitate bony on-growth with the spinal implant. In some embodiments, the spinal implant system includes a pedicle screw comprising an implant receiver, a compression ring and a threaded shaft.

In some embodiments, the spinal implant system of the present disclosure comprises a compression ring configured to improve fixation strength and/or bony-on growth with a bone screw. In some embodiments, the compression ring is disposed between a receiver and a head of the bone screw such that the compression ring is compressed therebetween. In some embodiments, the compression ring includes an outer surface such that at least a portion of the outer surface includes a coarse and/or roughened configuration. In some embodiments, the outer surface includes a porous layer. In some embodiments, the configuration of the outer surface enhances bony integration and resists and/or prevents bone screw toggle. In some embodiments, the compression ring may be coated with biologic agents to promote bony on-growth. In some embodiments, the compression ring includes a variable structure, such as, for example, any combination of solid, roughened surfaces, porous surfaces, honeycomb filled and/or structure having a trabecular configuration.

In some embodiments, the compression ring includes a porous or enhanced surface to promote bony on-growth. In some embodiments, the compression ring may be fabricated with an additive manufacturing method such that a roughened or porous structure is applied. In some embodiments, the compression ring may include coatings such as hydroxyapatite or tantalum to promote bony on-growth. In some embodiments, the compression ring may be fabricated with a subtractive manufacturing process, such as, for example, acid etching, shot peening, etc., to form a coarse surface on the outer surface.

In some embodiments, the compression ring may be utilized with a modular head bone screw system and engaged with a pedicle. In some embodiments, the compression ring is disposed with the screw and then the head component is attached. In some embodiments, this configuration facilitates use of a compression ring size with various diameter bone screws. In some embodiments, the spinal implant system of the present disclosure comprises a modular screw system including screw shaft assemblies, implant receiver/head assemblies and one or more compression rings that may be joined together during manufacturing or intraoperatively, such as, for example, during a surgical procedure in an operating room.

In some embodiments, fusion graft material may be added before or after the placement of the compression ring. In some embodiments, the surface of the compression ring facilitates retention of the biologics such that bone growth occurs to resist and/or prevent screw toggle. In some embodiments, captured cortical and/or cancellous bone is embedded with the compression ring as bone graft to facilitate promotion of bone growth and bone screw fusion. In some embodiments, external grafting materials or biologics may be prepacked with the compression ring.

In some embodiments, the compression ring is configured to mate with the head of the screw. In some embodiments, the compression ring is configured as a flat washer. In some embodiments, the compression ring is configured as a Belleville washer such that the ring is configured to deflect when a load is applied to increase resistance by applying a preload to the bone threads. In some embodiments, the compression ring is configured with a split such that the ring expands radially when compressed to increase contact with mating vertebral tissue.

In some embodiments, the spinal implant system of the present disclosure includes a compression ring fabricated via one or more additive manufacturing features and materials. In some embodiments, additive manufacturing includes 3-D printing. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing and on-demand manufacturing. The types of additive manufacturing that can be implemented for the present technology is not limited to these examples.

In some embodiments, the spinal implant system comprises one or more components, as described herein, of a spinal implant being manufactured by a fully additive process and grown or otherwise printed. In some embodiments, the compression ring of the present disclosure includes a non-solid portion, for example, a porous layer that is applied to the compression ring via additive manufacturing, for example, 3-D printing. In some embodiments, this configuration avoids compromising the integrity of a spinal construct and promotes bone fusion. In some embodiments, the compression ring is fabricated via a manufacturing method, such as, for example, one or more traditional manufacturing features and materials and a manufacturing method, such as, for example, one or more additive manufacturing features and materials.

In some embodiments, the spinal implant system of the present disclosure comprises a spinal implant, such as, for example, a bone screw manufactured by combining traditional manufacturing methods and additive manufacturing methods. In some embodiments, the bone screw is manufactured by applying additive manufacturing material in areas where the bone screw can benefit from materials and properties of additive manufacturing. In some embodiments, traditional materials are utilized where the benefits of these materials, such as physical properties and cost, are superior to those resulting from additive manufacturing features and materials.

In some embodiments, the spinal implants, surgical instruments and/or medical devices of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the spinal implants, surgical instruments and/or medical devices of the present disclosure may be employed with other osteal and bone related applications, including those associated with diagnostics and therapeutics. In some embodiments, the spinal implants, surgical instruments and/or medical devices of the present disclosure may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions such as maxillofacial and extremities. The spinal implants, surgical instruments and/or medical devices of the present disclosure may also be alternatively employed with procedures for treating the lumbar, cervical, thoracic, sacral and pelvic regions of a spinal column. The spinal implants, surgical instruments and/or medical devices of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
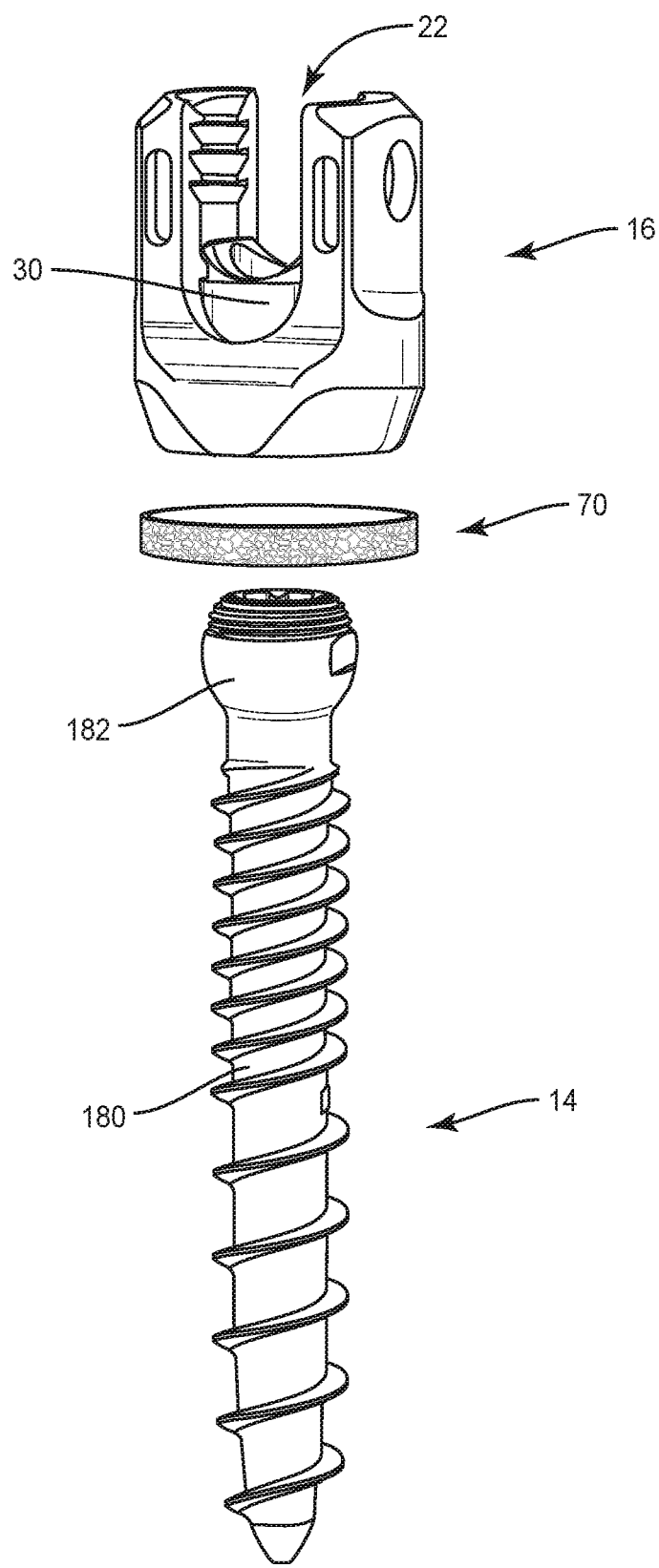
FIG. 2 is a side view, with parts separated, of the components shown in FIG. 1.
Figure 3:
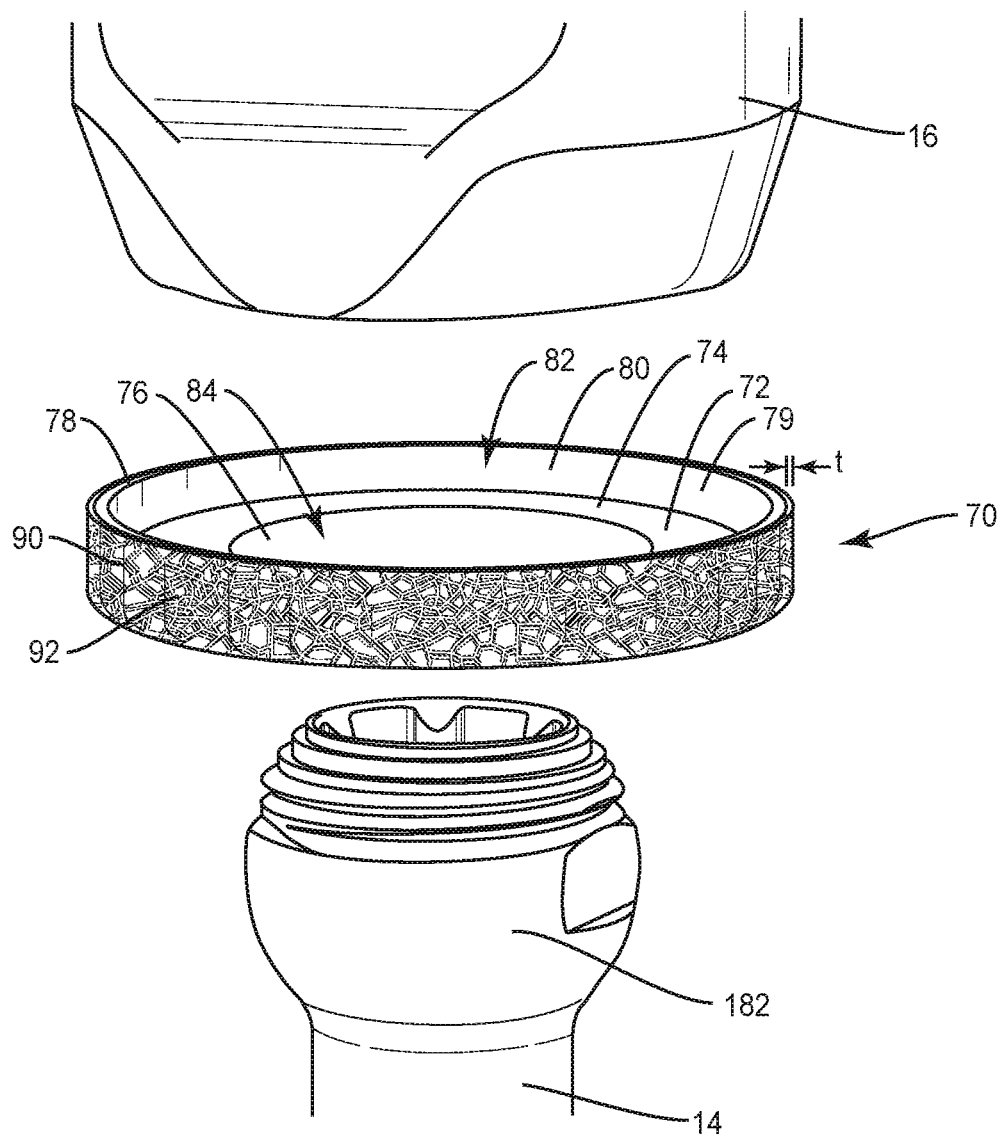
FIG. 3 is an enlarged, break away view of the components shown in FIG. 2.

The following discussion includes a description of a spinal implant, a method of manufacturing a spinal implant, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-3, there are illustrated components of a spinal implant system 10 including spinal implants, surgical instruments and medical devices.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 includes a spinal implant comprising a bone fastener, such as, for example, a bone screw 12. Bone screw 12 comprises a screw shaft 14, an implant receiver 16 and a ring or band, such as, for example a compression ring 70. Ring 70 includes a coarse surface configured to promote bone on-growth and enhance fixation of bone screw 12, as described herein.

Receiver 16 includes a pair of spaced apart arms 18, 20. Arms 18, 20 define implant cavity 22 therebetween, implant cavity 22 is configured for disposal of a component of a spinal construct, such as, for example, a spinal rod. Arms 18, 20 each extend parallel to an axis X1. In some embodiments, arm 18 and/or arm 20 may be disposed at alternate orientations, relative to axis X1, such as, for example, transverse, perpendicular and/or other angular orientations such as acute or obtuse, coaxial and/or may be offset or staggered. Arms 18, 20 each include an arcuate outer surface extending between a pair of side surfaces. At least one of the outer surfaces and the side surfaces of arms 18, 20 have at least one recess or cavity therein configured to receive an insertion tool, compression instrument and/or instruments for inserting and tensioning bone fastener 12. In some embodiments, arms 18, 20 are connected at proximal and distal ends thereof such that receiver 16 defines a closed spinal rod slot.

Cavity 22 is substantially U-shaped. In some embodiments, all or only a portion of cavity 22 may have alternate cross section configurations, such as, for example, closed, V-shaped, W-shaped, oval, oblong triangular, square, polygonal, irregular, uniform, non-uniform, offset, staggered, and/or tapered. Receiver 16 includes an inner surface 24. A portion of surface 24 includes a thread form located adjacent arm 18 and adjacent arm 20. The thread form is configured for engagement with a coupling member, such as, for example, a setscrew (not shown), to retain the spinal rod within cavity 22. In some embodiments, surface 24 may be disposed with the coupling member in alternate fixation configurations, such as, for example, friction fit, pressure fit, locking protrusion/recess, locking keyway and/or adhesive. In some embodiments, all or only a portion of surface 24 may have alternate surface configurations to enhance engagement with the spinal rod and/or the setscrew, such as, for example, rough, arcuate, undulating, mesh, porous, semi-porous, dimpled and/or textured. In some embodiments, receiver 16 may include alternate configurations, such as, for example, closed, open and/or side access.

In some embodiments, receiver 16 includes a surface configured for disposal of a crown 30. Crown 30 is configured for disposal within implant cavity 22. In some embodiments, crown 30 includes a curved portion configured for engagement with the spinal rod.

Ring 70 includes a body 72. Body 72 includes a circular configuration. Body 72 includes a surface 74 and a surface 76. Ring 70 includes a wall 78 circumferentially disposed about body 72, as shown in FIG. 3. Wall 78 includes a flange 79 that includes a surface 80. Surface 80 is disposed in communication with surface 74 and define a cavity 82. Cavity 82 is configured for disposal of a portion of receiver 16 such that surfaces 74, 80 matingly engage the portion of receiver 16. Receiver 16 is configured for disposal with cavity 82 such that receiver 16 compresses ring 70 between receiver 16 and tissue during use, as described herein. In some embodiments, ring 70 is configured as a washer. In some embodiments, ring 70 is configured as a conical spring washer.

Surface 76 defines a cavity 84 configured for disposal of a portion of head 182. Surface 76 matingly engages a portion of a head 182 of screw shaft 14. Surface 76 engages head 182 with ring 70 via a pressure and/or force fit connection. In some embodiments, surface 76 facilitates a non-instrumented assembly with ring 70 and head 182. In some embodiments, ring 70 may be disposed with head 182 in alternate fixation configurations, such as, for example, friction fit, pressure fit, locking protrusion/recess, locking keyway and/or adhesive. In some embodiments, ring 70 is configured for rotation relative to head 182. In some embodiments, ring 70 is configured for rotation in range of 360 degrees relative to head 182 to facilitate positioning of shaft 180 with tissue. In some embodiments, ring 70 is configured for selective rotation in range of 360 degrees relative to and about head 182 such that shaft 180 is selectively aligned for rotation in a plane relative to receiver 16 and ring 70.

Wall 78 includes an outer surface 90. Surface 90 includes a coarse and/or roughened configuration that is uneven or irregular to facilitate improved strength, bone on-growth of bone screw 12. In some embodiments, surface 90 includes a lattice extending along surface 90. In some embodiments, the lattice may include one or more portions, layers and/or substrates. Disclosures herein involving a porous, or other particular type of non-solid structure, are meant to disclose at the same time analogous embodiments in which other non-solid structure in addition or instead of the particular type of structure.

In some embodiments, surface 90 is configured for providing a fabrication platform for forming a layer 92 thereon. Layer 92 includes a thickness t, as shown in FIG. 3. In some embodiments, thickness t is in the range of about 0.5 mm to about 5.0 mm. In some embodiments, thickness t is in the range of about 0.5 mm to about 2.5 mm. In some embodiments, layer 92 may be formed by a coating of a material, such as, for example, HA or tantalum to promote bony on-growth. In some embodiments, the coating may be applied to layer 92 by to promote bony on-growth. In some embodiments, layer 92 may be fabricated by a subtractive process, such as, for example, acid etching, shot peening, etc., to produce the coarse configuration of surface 90. Any of a wide variety of subtractive processes, such as but not limited to any of various types of acid etching processes, and any of various types of shot-peening processes, can be implemented for achieving the functions and implant qualities of the present technology, as described herein.

In some embodiments, layer 92 is fabricated with a manufacturing method such as, for example, an additive manufacturing method, as described herein. Layer 92 is applied by disposing a material onto surface 90, as described herein. Layer 92 is applied circumferentially about surface 90. Layer 92 includes a non-solid configuration, such as, for example, a porous structure and/or a trabecular configuration. In some embodiments, all or only a selected portion of ring 70 includes a non-solid configuration, as described herein. In some embodiments, all or only a selected portion of ring 70 includes a non-solid configuration, as described herein, and is fabricated with an additive manufacturing method, as described herein.

In some embodiments, additive manufacturing includes 3-D printing, as described herein. In some embodiments, additive manufacturing includes fused deposition modeling, selective laser sintering, direct metal laser sintering, selective laser melting, electron beam melting, layered object manufacturing and stereolithography. In some embodiments, additive manufacturing includes rapid prototyping, desktop manufacturing, direct manufacturing, direct digital manufacturing, digital fabrication, instant manufacturing or on-demand manufacturing. In some embodiments, layer 92 is applied by additive manufacturing, as described herein, and mechanically attached with surface 90 by, for example, welding, threading, adhesives and/or staking. Any of a wide variety of additive processes can be implemented for achieving the functions and implant qualities of the present technology, as described herein, and are not limited to the examples mentioned or otherwise.

In various embodiments, layer 92 includes a non-solid configuration to facilitate bone through growth within, and in some embodiments all of the way through, from one surface to an opposite surface of bone screw 12. In some embodiments, one or more portions, layers and/or substrates of layer 92 may be disposed side by side, offset, staggered, stepped, tapered, end to end, spaced apart, in series and/or in parallel. In some embodiments, layer 92 defines a thickness, which may be uniform, undulating, tapered, increasing, decreasing, variable, offset, stepped, arcuate, angled and/or staggered. In some embodiments, layer 92 includes one or more layers of a matrix of material. In some embodiments, layer 92 includes one or a plurality of cavities, spaces and/or openings. In some embodiments, layer 92 may form a rasp-like configuration. In some embodiments, layer 92 is configured to engage tissue, such as, for example, cortical bone and/or cancellous bone, such as, to cut, shave, shear, incise and/or disrupt such tissue. In some embodiments, all or a portion of layer 92 may have various configurations, such as, for example, cylindrical, round, oval, oblong, triangular, polygonal having planar or arcuate side portions, irregular, uniform, non-uniform, consistent, variable, horseshoe shape, U-shape or kidney bean shape. In some embodiments, layer 92 may be rough, textured, porous, semiporous, dimpled, knurled, toothed, grooved and/or polished to facilitate engagement and cutting of tissue.

In some embodiments, layer 92 is fabricated according to instructions received from the computer and processor based on the digital rendering and/or data of the selected configuration, via the additive manufacturing process. See also, the examples and disclosure of the additive and three dimensional manufacturing systems and methods shown and described in commonly owned and assigned U.S. patent application Ser. No. 15/889,355 filed Feb. 6, 2018, and published as U.S. Patent Application Publication No. 10864602, on Dec. 15, 2020; and the examples and disclosure of the additive and three dimensional manufacturing systems and methods shown and described in commonly owned and assigned U.S. patent application Ser. No. 15/666, 305 filed Aug. 1, 2017, and published as U.S. Patent Application Publication No. 11229465, on Jan. 25, 2022 the entire contents of each of these references being hereby incorporated by reference herein in their respective entireties.

In one embodiment, one or more manufacturing methods for fabricating layer 92, all or only a selected portion of ring 70 and other components of bone screw 12, such as, for example, screw shaft 14 and receiver 16 include imaging patient anatomy with imaging techniques, such as, for example, x-ray, fluoroscopy, computed tomography (CT), magnetic resonance imaging (MRI), surgical navigation, bone density (DEXA) and/or acquirable 2-D or 3-D images of patient anatomy. Selected configuration parameters of screw shaft 14, receiver 16, ring 70 and layer 92 and/or other components of bone screw 12 are collected, calculated and/or determined. Such configuration parameters can include one or more of patient anatomy imaging, surgical treatment, historical patient data, statistical data, treatment algorithms, implant material, implant dimensions, porosity and/or manufacturing method. In some embodiments, the configuration parameters can include implant material and porosity of layer 80 determined based on patient anatomy and the surgical treatment. In some embodiments, the implant material includes a selected porosity of layer 92, as described herein. In some embodiments, the selected configuration parameters of screw shaft 14, receiver 16, all or only a selected portion of ring 70 and layer 92 and/or other components of bone screw 12 are patient specific. In some embodiments, the selected configuration parameters of screw shaft 14, receiver 16, all or only a selected portion of ring 70 and layer 92 and/or other components of bone screw 12 are based on generic or standard configurations and/or sizes and not patient specific. In some embodiments, the selected configuration parameters of screw shaft 14, receiver 16, all or only a selected portion of ring 70 and layer 92 and/or other components of bone screw 12 are based on one or more configurations and/or sizes of components of a kit of spinal implant system 10 and not patient specific.

Screw shaft 14 includes a shaft 180 is configured to penetrate tissue, such as, for example, bone. In some embodiments, shaft 180 includes an outer surface having an external thread form. In some embodiments, the external thread form may include a single thread turn or a plurality of discrete threads. Head 182 includes a tool engaging portion configured to engage a surgical tool or instrument, as described herein. In some embodiments, the tool engaging portion includes a hexagonal cross-section to facilitate engagement with a surgical tool or instrument, as described herein. In some embodiments, the tool engaging portion may have alternative cross-sections, such as, for example, rectangular, polygonal, hexalobe, oval, or irregular. In some embodiments, head 182 includes a plurality of ridges to improve purchase of head 182 with the crown. Head 182 is configured for attachment with ring 70 and receiver 16, as described herein.

In some embodiments, the external thread form is fabricated to include a fine, closely-spaced and/or shallow configuration to facilitate and/or enhance engagement with tissue. In some embodiments, the external thread form is fabricated to be continuous along shaft 180. In some embodiments, the external thread form is fabricated to be intermittent, staggered, discontinuous and/or may include a single thread turn or a plurality of discrete threads. In some embodiments, shaft 180 is fabricated to include penetrating elements, such as, for example, a nail configuration, barbs, expanding elements, raised elements, ribs, and/or spikes. In some embodiments, the external thread form is fabricated to be self-tapping or intermittent at a distal tip. In some embodiments, the distal tip may be rounded. In some embodiments, the distal tip may be self-drilling. In some embodiments, the distal tip includes a solid outer surface.

In some embodiments, receiver 16 and/or ring 70 is manually engageable with screw shaft 14 in a non-instrumented assembly, as described herein. In some embodiments, manual engagement and/or non-instrumented assembly of receiver 16 and screw shaft 14 includes coupling without use of separate and/or independent instrumentation engaged with screw shaft 14 components to effect assembly. In some embodiments, manual engagement and/or non-instrumented assembly includes a practitioner, surgeon and/or medical staff grasping receiver 16 and screw shaft 14 and forcibly assembling the components. In some embodiments, manual engagement and/or non-instrumented assembly includes a practitioner, surgeon and/or medical staff grasping receiver 16 and screw shaft 14 and forcibly snap fitting the components together, as described herein. In some embodiments, manual engagement and/or non-instrumented assembly includes a practitioner, surgeon and/or medical staff grasping receiver 16 and screw shaft 14 and forcibly pop fitting the components together and/or pop fitting receiver 16 onto screw shaft 14, as described herein. In some embodiments, a force in a range of 2-50 N is required to manually engage receiver 16 and screw shaft 14 and forcibly assemble the components. For example, a force in a range of 2-50 N is required to snap fit and/or pop fit assemble receiver 16 and screw shaft 14. In some embodiments, a force in a range of 5-10 N is required to manually engage receiver 16 and screw shaft 14 and forcibly assemble the components. For example, a force in a range of 5-10 N is required to snap fit and/or pop fit assemble receiver 16 and screw shaft 14. In some embodiments, screw shaft 14 is manually engaged with ring 70 and/or receiver 16 in a non-instrumented assembly, as described herein, such that removal of receiver 16 and screw shaft 14 requires a force and/or a pull-out strength of at least 5000 N. In some embodiments, this configuration provides manually engageable components that are assembled without instrumentation, and subsequent to assembly, the assembled components have a selected pull-out strength and/or can be pulled apart, removed and/or separated with a minimum required force. In some embodiments, spinal implant system 10 comprises a spinal implant kit, as described herein, which includes a plurality of screw shafts 14 and/or receivers 16.

In some embodiments, bone screw 12 can include various configurations, such as, for example, a posted screw, a pedicle screw, a bolt, a bone screw for a lateral plate, an interbody screw, a uni-axial screw, a fixed angle screw, a multi-axial screw, a side loading screw, a sagittal adjusting screw, a transverse sagittal adjusting screw, an awl tip, a dual rod multi-axial screw, midline lumbar fusion screw and/or a sacral bone screw.

In assembly, operation and use, spinal implant system 10 is employed to treat an affected section of vertebrae. A medical practitioner obtains access to a surgical site including the vertebrae in any appropriate manner, such as through incision and retraction of tissues. The components of spinal implant system 10 including bone screw 12 are employed to augment a surgical treatment. Bone screw 12 can be delivered to a surgical site as a pre-assembled device or can be assembled in situ. Spinal implant system 10 may be may be completely or partially revised, removed or replaced.

Surgical system 10 may be used with surgical methods or techniques including open surgery, mini-open surgery, minimally invasive surgery and percutaneous surgical implantation, whereby the vertebrae is accessed through a mini-incision, or sleeve that provides a protected passageway to the area. Once access to the surgical site is obtained, a surgical treatment, for example, corpectomy and/or discectomy, can be performed for treating a spine disorder.

Bone screw 12 is connected with a surgical instrument, such as, for example, a driver (not shown) and is delivered to the surgical site. Bone screw 12 is manipulated including rotation and/or translation for engagement with cortical bone and/or cancellous bone. Ring 70 is engaged with head 182 such that head 182 is disposed with cavity 84. Receiver 16 is manually engaged with screw shaft 14 in a non-instrumented assembly, as described herein. A portion of receiver 16 is disponed with cavity 82. Ring 70 is compressed between receiver 16 and bone. Bone screw 12 including ring 70 having layer 92 enhances fixation and/or facilitates bone on-growth, as described herein. In some embodiments, tissue becomes imbedded with layer 92 to promote bone on-growth, enhance fusion of bone screw 12 with vertebral tissue, and/or prevent toggle of bone screw 12 components.

It will be understood that various modifications may be made to the embodiments disclosed herein. Therefore, the above description should not be construed as limiting, but merely as exemplification of the various embodiments.

Those skilled in the art will envision other modifications within the scope and spirit of the claims appended hereto.

What is claimed is:

1. A bone screw comprising:
   a shaft including at least one thread having an external thread form;
   an implant receiver; and
   a ring including a body and a wall circumferentially disposed about the body, the ring including a flange extending from the wall, the flange defining a first mating surface, the wall and the flange defining a cavity, the implant receiver being disposed in the cavity such that the first mating surface engages the implant receiver, the wall including opposite proximal and distal surfaces and a substantially even outer surface extending from the proximal surface to the distal surface, the flange being flush with the distal surface, the proximal and distal surfaces each being planar about a circumference of the ring, at least a portion of the outer surface having a coarse configuration to promote tissue on-growth with the outer surface, the coarse configuration being fabricated from an additive manufacturing process.

2. A bone screw as recited in claim 1, wherein a portion of the outer surface includes a porous layer disposed thereon.

3. A bone screw as recited in claim 1, wherein a portion of the outer surface includes a coating disposed thereon.

4. A bone screw as recited in claim 3, wherein the coating includes HA.

5. A bone screw as recited in claim 3, wherein the coating includes tantalum.

6. A bone screw as recited in claim 1, wherein the coarse configuration is fabricated by a subtractive process.

7. A bone screw as recited in claim 6, wherein the subtractive process includes acid etching or shot peening.

8. A bone screw as recited in claim 1, wherein a portion of the outer surface includes a lattice configuration.

9. A bone screw as recited in claim 1, wherein a portion of the outer surface includes a trabecular configuration.

10. A bone screw as recited in claim 1, wherein the ring includes a compression ring.

11. A bone screw as recited in claim 1, wherein the ring includes a second mating surface engageable with a head of the shaft.

12. A bone screw as recited in claim 1, wherein the body has a circular configuration.

13. A bone screw comprising:
    a shaft comprising a head and a threaded portion;
    a receiver including opposite proximal and distal ends, the distal end defining an aperture configured for disposal of the head such that the shaft is rotatable relative to the receiver; and
    a ring including a wall and a flange extending from the wall, the flange defining a first mating surface, the flange and the wall defining a cavity having the distal end disposed therein such that the distal end directly engages the first mating surface, the wall including a substantially even outer surface, at least a portion of the outer surface having a coarse configuration to promote tissue on-growth with the outer surface, the course configuration being fabricated by an additive manufacturing process, the wall including opposite proximal and distal surfaces, the flange being flush with the distal surface, the outer surface extending perpendicular to the proximal and distal surfaces from the proximal surface to the distal surface, the proximal and distal surfaces each being planar about a circumference of the ring.

14. A bone screw as recited in claim 13, wherein the additive manufacturing process includes 3-D printing.

15. A bone screw as recited in claim 13, wherein the flange includes an even, uninterrupted surface relative to the outer surface.

16. A bone screw as recited in claim 13, wherein the outer surface includes a porous layer.

17. A bone screw as recited in claim 13, wherein the outer surface includes a lattice.

18. A bone screw comprising:
    a shaft including at least one thread having an external thread form;
    an implant receiver having opposite proximal and distal ends; and
    a monolithic ring including a wall and a flange extending from the wall, the flange defining a first mating surface, the wall defining a second mating surface extending perpendicular to the first mating surface, the flange and the wall defining a cavity having the distal end disposed therein such that the distal end directly engages the mating surfaces, the wall including an outer surface, at least a portion of the outer surface having a coarse configuration to promote tissue on-growth with the outer surface, the coarse configuration being fabricated from an additive manufacturing process, the wall having a uniform thickness about a circumference of the ring, the wall including opposite proximal and distal surfaces, the flange being flush with the distal surface, the outer surface extending perpendicular to the proximal and distal surfaces from the proximal surface to the distal surface, the proximal and distal surfaces each being planar about the circumference of the ring.

19. A bone screw as recited in claim 18, wherein the outer surface is substantially even.

* * * * *